(12) United States Patent
Garel et al.

(10) Patent No.: US 10,544,081 B2
(45) Date of Patent: Jan. 28, 2020

(54) PROCESS FOR PREPARING MANDELIC AROMATIC COMPOUNDS AND AROMATIC ALDEHYDE COMPOUNDS

(71) Applicant: RHODIA OPERATIONS, Paris (FR)

(72) Inventors: Laurent Garel, Lyons (FR); Flavie Sarrazin, Talence (FR); Olivier Back, Lyons (FR); Kevin Olivon, Anglet (FR); Mathieu Pucheault, Camblanes et Meynac (FR)

(73) Assignee: RHODIA OPERATIONS, Paris (FR)

( * ) Notice: Subject to any disclaimer, the term of this patent is extended or adjusted under 35 U.S.C. 154(b) by 48 days.

(21) Appl. No.: 15/036,871

(22) PCT Filed: Nov. 14, 2014

(86) PCT No.: PCT/EP2014/074658
§ 371 (c)(1),
(2) Date: May 16, 2016

(87) PCT Pub. No.: WO2015/071431
PCT Pub. Date: May 21, 2015

(65) Prior Publication Data
US 2016/0297735 A1  Oct. 13, 2016

(30) Foreign Application Priority Data
Nov. 15, 2013 (FR) ...................... 13 61169

(51) Int. Cl.
*C07C 51/367* (2006.01)
*C07C 45/39* (2006.01)

(52) U.S. Cl.
CPC ............ *C07C 51/367* (2013.01); *C07C 45/39* (2013.01)

(58) Field of Classification Search
None
See application file for complete search history.

(56) References Cited

U.S. PATENT DOCUMENTS

| | | | |
|---|---|---|---|
| 2,640,083 A | 5/1953 | Kamlet | |
| 4,048,236 A * | 9/1977 | Nagai | C07C 43/215 568/652 |
| 4,190,583 A | 2/1980 | Bauer et al. | |
| 4,978,784 A | 12/1990 | Christidis | |
| 5,430,183 A * | 7/1995 | Nobel | C07C 51/367 562/478 |
| 6,359,172 B1 * | 3/2002 | Kessels | C07C 51/367 562/470 |
| 9,018,421 B2 | 4/2015 | Gayet et al. | |
| 2011/0306802 A1 | 12/2011 | Maliverney et al. | |

FOREIGN PATENT DOCUMENTS

| | | |
|---|---|---|
| EP | 0368696 B1 | 6/1992 |
| EP | 0987245 A1 | 3/2000 |
| EP | 1206318 B1 | 2/2005 |
| JP | S5620538 A | 2/1981 |
| JP | S59-098033 A | 6/1984 |
| JP | 2004-269451 A | 9/2004 |
| WO | 2008148760 A2 | 12/2008 |
| WO | 2010007161 A1 | 1/2010 |

OTHER PUBLICATIONS

Niu, Dong-Fang, et al—"Improved synthesis of 3-methoxy-4-hydrocymandelic acid by glyoxalic acid method", 2013, Tetrahedron, vol. 69, Issue No. 3, pp. 8174-8177, XP028688564.
Firouzabadi, H., et al—"Bis(2,2'-bipyridyl)copper(II) permanganate (BBCP): A mild and versatile oxidant in organic sysnthesis", 1984, Tetrahedron, vol. 40, Issue No. 23, pp. 5001-5004, XP 055162855.
Telvekar, Vikas, et al—"Oxidative Decarboxylation of 2-Aryl carboxylic Acids Using (Diacetoxyiodo) benzene for Preparation of Aryl Aldehyds, Ketones, and Nitriles", 2010, Synlett, vol. 2010, Issue No. 18, Thieme Stuttgart, NY, pp. 2778-2780, XP 055162862.
Higuchi, Masayoshi, et al—"A Novel Synthetic Metal Catalytic System", 1997, The Journal of Organic Chemistry, vol. 62, Issue No. 4, pp. 1072-1078, XP 055162868.
Firouzabadi, H., et al—"Dinitratocerium (IV) Chromate Dihydrate, <Ce(N03)2> Cr04*2H20, A Mild Reagent For The Oxidation of Organic Compounds in Organic Media", 1984, Synthetic Communications, vol. 14, Issue No. 10, pp. 973-981, XP 8174247.
Hoefnagel, A.J., et al—"Separation of 2- and 4-hydroxymandelic acid", 1996, Recueil Des Travaux Chimiques Des Pays-Bas, vol. 115, 7-8 Jul./Aug. 1996, pp. 353-356, XP 055126038.
Higuchi, Masayoshi, et al., A Novel Synthetic Metal Catalytic System; J. Org. Chem., 1997, vol. 62, No. 4, pp. 1072-1078.

* cited by examiner

*Primary Examiner* — Sudhakar Katakam
*Assistant Examiner* — Jennifer C Sawyer
(74) *Attorney, Agent, or Firm* — Osha Liang LLP

(57) ABSTRACT

A process for preparing an aromatic compound or compounds where at least one mandelic group —CHOH—COOH is described, comprising a reaction for condensation of at least one aromatic compound with glyoxylic acid or derivatives thereof, wherein said condensation reaction is carried out substantially in the absence of any acid or any base added to the reaction medium. The condensation reaction is followed by an oxidation reaction in order to obtain aromatic aldehyde.

18 Claims, No Drawings

PROCESS FOR PREPARING MANDELIC AROMATIC COMPOUNDS AND AROMATIC ALDEHYDE COMPOUNDS

This application is a U.S. national stage entry under 35 U.S.C. § 371 of International Patent Application No. PCT/EP2014/074658, filed Nov. 14, 2014, which claims priority to French Application No. 1361169, filed on Nov. 15, 2013, the whole content of each of these applications is hereby incorporated herein by reference for all purposes.

The present invention relates to the field of the preparation of mandelic aromatic compounds and of aromatic aldehyde compounds obtained from said mandelic aromatic compounds. More particularly, the present invention relates to the preparation of hydroxymandelic aromatic compounds and to the preparation of hydroxyaromatic aldehyde compounds.

In the account which follows of the invention, the mandelic group is understood by the —CHOH—COOH group, which is present as substituent on the aromatic nucleus of said mandelic aromatic compounds.

The present invention is more particularly targeted at the preparation of p-hydroxymandelic acid, 4-hydroxy-3-methoxymandelic acid and 3-ethoxy-4-hydroxymandelic acid, and also at the preparation of vanillin and/or ethylvanillin.

Vanillin is obtained from natural sources, such as lignin or ferulic acid, but a substantial proportion of vanillin and its derivatives is produced via the chemical route. Numerous diverse and varied preparation methods are described in the literature (Kirk-Othmer—Encyclopedia of Chemical Technology, 24, pp 812-825, 4th edition (1997)). A conventional access route to vanillin and its derivatives involves a condensation reaction of glyoxylic acid with guaiacol in a basic aqueous medium, in order to obtain 4-hydroxy-3-methoxy-mandelic acid. This product is subsequently oxidized in a basic medium to give vanillin. This conventional process is, for example, employed in the U.S. Pat. No. 2,640,083, which describes the condensation of guaiacol and sodium glyoxylate obtained by reaction of glyoxylic acid with sodium hydroxide.

This conventional process, carried out in a basic medium, results in an unfavorable reaction consisting of the disproportionation of glyoxylic acid according to the known Cannizzaro reaction (production of glycolic acid and oxalic acid). This parallel reaction substantially affects the yield and the selectivity of the condensation reaction. Furthermore, carrying out condensation and oxidation reactions in a basic medium suffers because of the need to carry out neutralization stages by the use of a strong acid, generally sulfuric acid, both after carrying out the condensation reaction and after the condensation reaction. In point of fact, said neutralization stages generate a considerable amount of salts, generally sulfate salts, in particular in the form of sodium sulfate $Na_2SO_4$ salts, which it is advisable to subsequently treat. Neither does carrying out the condensation reaction in a highly dilute aqueous medium favor the treatment of the salified, generally sulfated, aqueous effluents at the outlets of the condensation and oxidation reactors.

Patent application EP 0 987 245 describes a process for the condensation of phenol and glyoxylic acid in the presence of an anion-exchange resin. However, the presence of this basic resin does not make it possible to solve the problem of the management of the aqueous effluents. This is because a large amount of acidic, basic or saline solution has to be used as eluent in order to recover the hydroxymandelic acid formed.

Another major disadvantage of the prior process described above lies in carrying out the condensation reaction with an excess of guaiacol, which requires a stage of recycling of this reactant.

A subject matter of the present invention is a process for the preparation of mandelic aromatic compound(s) and of aromatic aldehyde compound(s) which makes it possible to overcome the disadvantages encountered in the prior process. In particular, the process provided by the applicant company is not carried out, or is only partially carried out, in an alkaline medium and thus avoids the need to carry out at least one of the neutralization stages subsequent to the condensation and oxidation reactions. The process according to the present invention thus exhibits the major advantage of generating an amount of salts which is considerably reduced, indeed even of not generating any salt at any stage of the process. In particular, the process of the invention does not generate any sulfate salt when neither the condensation reaction nor the oxidation reaction is carried out in a basic medium. The condensation reaction is also advantageously carried out in the absence of solvent, in particular in the absence of water, which thus avoids the treatment of a large amount of aqueous effluents downstream of the process and a saving at the level of the installation of the process and of the items of equipment funded. The process according to the invention, carried out under mild conditions, in the absence of an alkaline agent (at least for one or other of the condensation or oxidation reactions, preferably for both reactions) and preferably in the absence of water, at least as regards the condensation reaction, is thus more environmentally friendly.

A subject matter of the present invention is a process for the preparation of aromatic compound(s) carrying at least one mandelic —CHOH—COOH group comprising a condensation reaction of at least one aromatic compound with glyoxylic acid or its derivatives, said condensation reaction being carried out substantially in the absence of any acid or any base added to the reaction medium.

In addition, a subject matter of the present invention is a process for the preparation of aromatic compound(s) carrying at least one mandelic —CHOH—COOH group comprising a condensation reaction of at least one aromatic compound with glyoxylic acid or its derivatives, said condensation reaction being carried out in the absence of solvent and the glyoxylic acid being glyoxylic acid monohydrate.

Another subject matter of the present invention is a process for the preparation of aromatic compound(s) carrying at least one mandelic —CHOH—COOH group comprising a condensation reaction of at least one aromatic compound with glyoxylic acid or its derivatives, said condensation reaction being carried out in the presence of at least one catalyst chosen from transition metal complexes comprising oxygen-comprising ligands.

In accordance with the invention, said aromatic compound employed as reactant in the condensation reaction is advantageously chosen from substituted benzenes, phenol and substituted phenols, heterocyclic aromatic compounds or polycyclic aromatic compounds.

Among heterocyclic aromatic compounds, 1,3-benzodioxole, 1-methylindole and benzofuran are preferred. Among polycyclic aromatic compounds, naphthol is preferred. The substituted benzenes are preferably benzenes substituted by one or more groups chosen from an alkyl, alkenyl, alkoxy, hydroxyalkyl, alkoxyalkyl, cycloalkyl, aryl or arylalkyl group, a hydroxyl group, a nitro group, a halogen atom, a halo- or perhaloalkyl group, a formyl group, an acyl group having from 2 to 6 carbon atoms, a carboxyl group, or an amino or amido group substituted or unsubstituted by one or two alkyl or phenyl groups. It should be noted that the carboxyl group can be esterified, for example with an alkyl or phenyl group. Preferably, the substituted benzenes are benzenes substituted by one or more alkoxy groups, such as methoxy, ethoxy, propoxy, isopropoxy, butoxy or isobutoxy. Very preferably, the substituted benzenes are benzenes substituted by one, two or three methoxy groups. They are respectively methoxybenzene (anisole), 1,2-dimethoxybenzene (veratrole) and 1,2,3-trimethoxybenzene.

In accordance with the invention, the aromatic compound is preferably chosen from substituted phenols. Advantageously, said substituted phenols exhibit at least one unsubstituted position in the para position with respect to the hydroxyl group. The substituted phenols are molecules in which the aromatic nucleus carries at least one hydroxyl group and also carries one or more other substituents. Generally, the term "several substituents" defines from 2 to 4 substituents per aromatic nucleus. Any substituent can be present insofar as it does not interfere in the condensation reaction.

Thus, the process for the preparation of aromatic compound(s) carrying at least one mandelic group according to the invention is well suited to being applied to the substituted phenols corresponding to the following formula (I):

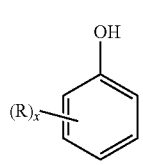
(I)

in said formula:
R represents one or more identical or different substituents,
x, the number of substituents on a ring, is an integer between 1 and 4,
when x is greater than 1, two R groups placed on two vicinal carbon atoms can form, together and with the carbon atoms which carry them, a saturated, unsaturated or aromatic ring having from 5 to 7 atoms and optionally comprising one or more heteroatoms.

In said formula (I), the position para to the hydroxyl group is preferably free, that is to say devoid of a substituent.

In the formula (I), the R groups, which are identical or different, represent an alkyl, alkenyl, alkoxy, hydroxyalkyl, alkoxyalkyl, cycloalkyl, aryl or arylalkyl group, a hydroxyl group, a nitro group, a halogen atom, a halo- or perhaloalkyl group, a formyl group, an acyl group having from 2 to 6 carbon atoms, a carboxyl group, or an amino or amido group substituted or unsubstituted by one or two alkyl or phenyl groups. It should be noted that the carboxyl group can be esterified, for example with an alkyl or phenyl group.

In the formula (I), when x is greater than 1, two R groups placed on two vicinal carbon atoms can be linked together via an alkylene, alkenylene or alkenylidene group having from 3 to 5 carbon atoms to form a saturated, unsaturated or aromatic ring having from 5 to 7 atoms, it being possible for one or more (preferably 2 or 3) carbon atoms to be replaced with a heteroatom, preferably oxygen.

In the formula (I), the term "alkyl" is understood to mean a linear or branched hydrocarbon chain having from 1 to 15 carbon atoms and preferably from 1 or 2 to 10 carbon atoms.

The term "alkoxy" is understood to mean an alkyl-O— group in which the term "alkyl" has the meaning given above. Preferred examples of alkoxy groups are the methoxy or ethoxy groups. The term "alkenyl" is understood to mean a linear or branched hydrocarbon group having from 2 to 15 carbon atoms, comprising one or more double bonds, preferably from 1 to 2 double bonds. The term "cycloalkyl" is understood to mean a cyclic hydrocarbon group comprising from 3 to 8 carbon atoms, preferably a cyclopentyl or cyclohexyl group. The term "aryl" is understood to mean a mono- or polycyclic, preferably mono- or bicyclic, aromatic group comprising from 6 to 12 carbon atoms, preferably phenyl or naphthyl. The term "arylalkyl" is understood to mean a linear or branched hydrocarbon group carrying a monocyclic aromatic ring and comprising from 7 to 12 carbon atoms, preferably benzyl. The term "halo- or perhaloalkyl" is understood to mean one of the following groups: —$CX_3$, —$[CX_2]_p$—$CX_3$ or —$C_pH_aF_b$—; in said groups, X represents a halogen atom, preferably a chlorine or fluorine atom, p represents a number ranging from 1 to 10, b represents a number ranging from 3 to 21 and a+b=2p+1.

In the case where x is greater than 1, two R groups placed on two vicinal carbon atoms can be linked together via an alkylene, alkenylene or alkenylidene group to form a saturated, unsaturated or aromatic ring having from 5 to 7 atoms, thus forming a bicycle. Examples of preferred bicyclic backbones are as follows:

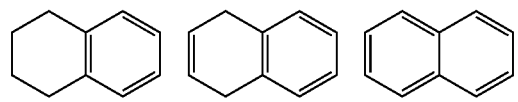

The compounds which are particularly well-suited to the implementation of the preparation process according to the invention correspond to the formula (I) in which R, which are identical or different, represent:
a hydroxyl group,
a linear or branched alkyl group having from 1 to 6 carbon atoms and preferably from 1 to 4 carbon atoms, such as methyl, ethyl, n-propyl, isopropyl, n-butyl, isobutyl, sec-butyl or tert-butyl,
a linear or branched alkenyl group having from 2 to 6 carbon atoms and preferably from 2 to 4 carbon atoms, such as vinyl or allyl,
a linear or branched alkoxy group having from 1 to 6 carbon atoms and preferably from 1 to 4 carbon atoms, such as the methoxy, ethoxy, n-propoxy, isopropoxy, n-butoxy, isobutoxy, sec-butoxy or tert-butoxy groups,
a phenyl group,
a halogen atom, preferably a fluorine, chlorine or bromine atom.

As regards the definition of x, x is advantageously equal to 1 or 2 and more preferably equal to 1.

The invention preferably applies to the compounds corresponding to the formula (I) in which R represents an alkyl group having from 1 to 4 carbon atoms and x is equal to 1 or also an alkoxy group having from 1 to 4 carbon atoms and x is equal to 1.

Mention may be made, by way of illustration of compounds corresponding to the formula (I), of:
those corresponding to the formula (I) in which x is equal to 1, such as:
pyrocatechol
resorcinol
hydroquinone o-cresol
m-cresol
2-ethylphenol
3-ethylphenol
2-propylphenol
2-(sec-butyl)phenol
2-(tert-butyl)phenol
3-(tert-butyl)phenol
2-methoxyphenol (guaiacol)
3-methoxyphenol
2-ethoxyphenol (guaethol)
2-isopropoxyphenol
salicylaldehyde
methyl salicylate
salicylic acid
2-chlorophenol
3-chlorophenol
3-nitrophenol
4-phenylphenol those corresponding to the formula (I) in which x is equal to 2, such as:
2,3-dimethylphenol (2,3-xylenol)
2,5-dimethylphenol (2,5-xylenol)
3,5-dimethylphenol (3,5-xylenol)
2-hydroxy-5-acetamidobenzaldehyde
2-hydroxy-5-ethamidobenzaldehyde
2,3-dichlorophenol
2,5-dichlorophenol
3,5-dichlorophenol
pyrogallol those corresponding to the formula (I) in which x is equal to 3, such as:
2,3,5-trimethylphenol
3,5-di(tert-butyl)phenol
2,3,5-trichlorophenol those corresponding to the formula (I) exhibiting a naphthalene group, such as:
1-naphthol
2-naphthol
1,2-dihydroxynaphthalene
1,5-dihydroxynaphthalene
2,3-dihydroxynaphthalene
2,6-dihydroxynaphthalene
2,7-dihydroxynaphthalene
6-bromo-2-naphthol those corresponding to the formula (I) exhibiting a sequence of benzene nuclei:
2-phenoxyphenol
3-phenoxyphenol Among the list of the abovementioned compounds, the substituted phenols employed are preferably: o-cresol, m-cresol, 3-ethylphenol, 2-(tert-butyl)phenol, guaiacol or guaethol.

The compounds to which the process for the preparation of an aromatic compound carrying at least one mandelic group according to the invention preferably applies are guaiacol and guaethol.

In accordance with the preparation process according to the invention, a condensation reaction of at least one of said aromatic compounds described above with glyoxylic acid or its derivatives is carried out. The glyoxylic acid employed in the condensation reaction can be used in all its forms, in particular in the solid form or in the form dissolved in an aqueous solution. Use is advantageously made of glyoxylic acid in the monohydrate form, $(CHO-CO_2H.H_2O)$. The derivatives of glyoxylic acid are understood in particular to mean esters of glyoxylic acid, such as the methyl and ethyl esters of glyoxylic acid.

It is understood that the alkali metal salts of glyoxylic acid, in particular sodium glyoxylate, are not included among the glyoxylic acid derivatives according to the present invention. Alkali metal glyoxylates are conventionally obtained by reaction of glyoxylic acid with an alkali metal base in an aqueous medium. In point of fact, the process according to the invention is carried out in the absence of added base. The use of glyoxylic acid salt requires carrying out neutralization stages by the use of a strong acid, and generates a considerable amount of salts.

According to one embodiment of the present invention, the condensation reaction is carried out without catalyst. In this case, the reaction is preferably carried out in the absence of solvent. Glyoxylic acid monohydrate can be used as reactant.

According to another embodiment, the process for the preparation of an aromatic compound carrying at least one mandelic —CHOH—COOH group according to the invention is advantageously carried out in the presence of at least one catalyst. Said catalyst is added to the reaction medium in a catalytic amount. Said catalytic process can operate by homogeneous catalysis or by heterogeneous catalysis, preferably by homogeneous catalysis. It is carried out in the presence of at least one catalyst preferably chosen from the group consisting of compounds based on transition metals and on rare earth metals, zeolites, clays, lanthanum phosphate ($LaPO_4$), metal oxides, in particular alkaline earth metal oxides, and metal hydroxides. The catalysts based on transition metals are advantageously chosen from transition metal complexes comprising oxygen-comprising ligands. The preferred transition metals are iron and copper. Zinc can also be used. The catalysts very advantageously employed in carrying out the preparation process according to the invention are iron(II) acetate ($Fe(OAc)_2$) and iron(III) acetate ($Fe(OAc)_3$), copper(II) acetate ($Cu(OAc)_2$), iron(II) acetylacetonate ($Fe(acac)_2$) and iron(III) acetylacetonate ($Fe(acac)_3$), copper(II) acetylacetonate ($Cu(acac)_2$) and copper (III) acetylacetonate ($Cu(acac)_3$) and their mixtures. The glyoxylate and the triflates are also advantageously employed as oxygen-comprising ligands.

The catalyst can be a complex composed of a transition metal, preferably iron or copper, and of at least one glyoxylate ligand. This complex can be formed in situ, when the catalyst based on a transition metal is brought into contact with the reaction medium containing the glyoxylic acid. Alternatively, this complex can be prepared prior to the condensation reaction. The process according to the invention can comprise a stage, prior to the condensation reaction, which consists in mixing a compound based on transition metals with glyoxylic acid. This mixture is subsequently brought into contact with at least one aromatic compound in the condensation reaction according to the invention.

Generally, the catalytic compound can be formed in situ during the condensation reaction. For this reason, the term "catalyst" can also broadly comprise the precursors of these catalytic compounds.

According to the preparation process of the invention, the condensation reaction is carried out substantially in the absence of any acid and of any base other than those constituted by the reactants and the catalyst, that is to say that no acid or base is substantially introduced into the reaction medium other than the acids and bases constituted by the reactants and the catalyst. The term "substantially", as regards the introduction of the base, should be understood as meaning that the base/Σ(acids present in the reaction medium) ratio is less than 10 mol %, preferably less than 5 mol %. The term "substantially", as regards the introduction of the acid, should be understood as meaning that the Σacid(s)/reactants ratio, in particular the Σacid(s)/(aromatic compound+glyoxylic acid or its derivatives) ratio, is less than 10 mol %, preferably less than 5 mol %. Preferably, the condensation reaction is carried out in the absence of any acid and of any base other than those constituted by the reactants and the catalyst, that is to say that no acid or base is introduced into the reaction medium other than the acids and bases constituted by the reactants and the catalyst. Preferably, the reaction medium does not contain an inorganic base or an organic base, and the reaction medium preferably does not contain NaOH, KOH or ammonium hydroxide.

In accordance with the process for the preparation of an aromatic compound carrying at least one mandelic group according to the invention, the condensation reaction is carried out in the liquid phase or in the liquid-solid phase. Said reaction is carried out in the presence or in the absence of solvent.

According to one embodiment, the reaction is carried out in the absence of solvent. In this case, glyoxylic acid monohydrate can be used as reactant. The water which can be released by the glyoxylic acid monohydrate cannot be regarded as a solvent insofar as its amount is negligible. Glyoxylic acid monohydrate is solid up to approximately 50° C. The temperature of the condensation reaction can advantageously be between 30° C. and 80° C., preferably between 40° C. and 60° C. and more preferably still between 45° C. and 50° C., and the reaction medium is preferably placed under stirring throughout the duration of the reaction in order to provide sufficient homogenization of the medium.

According to another embodiment, the reaction is carried out in the presence of a solvent. When it is carried out in the presence of a solvent, said solvent is, for example, water, an alcohol, in particular ethanol, an aromatic hydrocarbon, such as xylene, or also a water-alcohol mixture, for example a water-ethanol mixture, or else an ionic liquid, for example an ionic liquid chosen from quaternary ammonium salts (for example tetrabutylammonium salts), phosphonium salts (for example tetrabutylphosphonium salts), imidazolium salts (for example 1-alkyl-2,3-dimethylimidazolium salts or 1-alkyl-3-methylimidazolium salts) and pyridinium salts (for example 1-alkylpyridinium salts).

The condensation reaction consists in reacting glyoxylic acid or its derivatives with at least one aromatic compound as defined above. The molar ratio of the aromatic compound to glyoxylic acid or its derivatives preferably varies between 0.1 and 4.0, more preferably between 0.5 and 2 and more preferably still it is in the vicinity of 1 (that is to say, between 0.9 and 1.1), so that the equimolar ratio of said aromatic compound to glyoxylic acid or its derivatives avoids the recycling of one or other of said reactants.

When the condensation reaction is carried out by homogeneous catalysis, the amount of catalyst employed, expressed by the ratio of the number of moles of catalyst to the number of moles of glyoxylic acid (or its derivatives) or of aromatic compound (this introduced in a lower amount, i.e. the limiting reactant), is advantageously chosen between 0.5 and 30%, very advantageously between 0.5 and 10% and preferably between 1 and 3%.

When the condensation reaction is carried out by heterogeneous catalysis, the amount of catalyst employed, expressed by the ratio by weight of the weight of catalyst to the weight of the reaction medium, is advantageously chosen between 0.5 and 10 weight %, preferably between 1 and 3 weight %.

The temperature of the condensation reaction is advantageously chosen between 0° C. and 100° C. and preferably between 15° C. and 80° C.

The duration of the condensation reaction is between 1 minute and 24 hours. The reaction medium is preferably placed under stirring throughout the duration of the reaction.

The condensation reaction is carried out under pressure or at atmospheric pressure, under air or under a controlled atmosphere of inert gases, preferably of nitrogen or optionally of rare gases, in particular argon. Air is preferably chosen.

The process for the preparation of an aromatic compound carrying at least one mandelic group according to the invention can be carried out batchwise, semi-continuously or continuously.

The condensation reaction can be carried out in different types of reactors, for example in a tubular reactor (plug-flow reactor) or also in a cascade of perfectly stirred reactors.

A preferred form of the process for the preparation of an aromatic compound carrying at least one mandelic group consists in carrying out the condensation reaction of glyoxylic acid with guaiacol or the condensation reaction of glyoxylic acid with guaethol or also the condensation reaction of glyoxylic acid with guaiacol and guaethol. In the first two cases, the condensation reaction results in the production of a p-hydroxymandelic acid substituted in the ortho position with respect to the hydroxyl group respectively by a methoxy group (condensation of glyoxylic acid with guaiacol) and by an ethoxy group (condensation of glyoxylic acid with guaethol). In the third case, the condensation reaction of glyoxylic acid with guaiacol and guaethol results in the coproduction of a p-hydroxymandelic acid substituted in the ortho position with respect to the hydroxyl group by a methoxy group and of a p-hydroxymandelic acid substituted in the ortho position with respect to the hydroxyl group by an ethoxy group.

One embodiment of the preparation process according to the invention advantageously consists in introducing glyoxylic acid and the catalyst to said aromatic compound(s). The reaction medium is placed under stirring, for a period of time and at a temperature which are chosen within the above-mentioned intervals. The reaction medium obtained on conclusion of the condensation reaction contains the mandelic aromatic compound(s) in the acid form or in the mandelic ester form, when an ester of glyoxylic acid is employed as reactant. Said reaction medium is substantially devoid of salt, preferably entirely devoid of salt.

According to a preferred embodiment of the invention, the products obtained on conclusion of the condensation are separated. At the end of the condensation reaction, the mandelic aromatic compound(s) obtained, preferably a p-hydroxymandelic acid, is/are separated from the reaction mixture according to conventional separation techniques, in particular by crystallization or by extraction using an appropriate organic solvent.

According to a preferred embodiment of the process of the invention consisting in employing at least one substituted phenol of formula (I), the para position of which is free (that is to say, unsubstituted), as aromatic compound for carrying out said condensation reaction, the substituted hydroxymandelic compound(s) obtained on conclusion of said condensation reaction can be represented by the following formula (II):

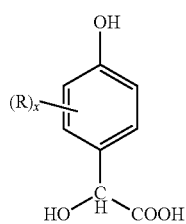

(II)

R and x having, in said formula (II), the meanings given in the formula (I).

The aromatic compounds carrying at least one mandelic group prepared according to the process of the invention are particularly advantageous as these are intermediate products which make it possible, inter alia, to obtain, by reduction, arylacetic acids, preferably hydroxyarylacetic acids, or, by oxidation, arylglyoxylic (=aryl-α-oxoacetic) acids, preferably hydroxyarylglyoxylic (=hydroxyaryl-α-oxoacetic) acids, or aromatic aldehydes, preferably hydroxyaromatic aldehydes.

Another subject matter of the invention is thus a process for the preparation of aromatic aldehyde(s) comprising the condensation reaction as described above in the present description, resulting in the preparation of mandelic compound(s), followed by an oxidation reaction of said mandelic compound(s). More preferably, when said aromatic compound employed in said condensation reaction is a substituted phenol of formula (I), the para position of which is free, a subject matter of the invention is more particularly a process for the preparation of 4-hydroxyaromatic aldehyde. More specifically, a subject matter of the invention is a process for the preparation of vanillin (VA or 4-hydroxy-3-methoxybenzaldehyde) and/or of ethylvanillin (EVA or 3-ethoxy-4-hydroxybenzaldehyde).

The term "oxidation" is understood here as an oxidative decarboxylation insofar as it comprises the departure of a carboxylic group, forming carbon dioxide.

The oxidation reaction employed for carrying out the process for the preparation of an aromatic aldehyde according to the invention is advantageously carried out in the presence of oxygen or air. Said oxidation reaction is carried out at atmospheric pressure or under pressure. It is carried out either with addition of alkaline agent or without addition of alkaline agent. Preferably, it is carried out without addition of alkaline agent, that is to say that no base is introduced into the reaction medium subjected to the oxidation reaction. Said oxidation reaction is generally carried out in the presence of a solvent, which can be organic or aqueous. Water is advantageously used as solvent. An ionic liquid can also be used as solvent. Preferred ionic liquids are those already mentioned above for carrying out the condensation reaction. However, the presence of a solvent is not necessary. It is carried out at a temperature preferably of between 10 and 200° C. On conclusion of said oxidation reaction, a crude aqueous reaction medium containing said aromatic aldehyde(s) is generally recovered.

Said oxidation reaction is carried out in the presence of a catalyst advantageously chosen from chromium, cobalt, copper, vanadium, manganese, iron, nickel and osmium derivatives. Preferably, vanadium and copper derivatives are chosen and, preferably, the catalyst employed for carrying out said oxidation reaction is ammonium metavanadate ($NH_4VO_3$) or vanadium oxide $V_2O_5$.

The oxidation reaction can be carried out batchwise, semi-continuously or continuously. It can be carried out in different types of reactors, for example in a tubular reactor (plug-flow reactor) or also in a cascade of perfectly stirred reactors.

A preferred embodiment of the process for the preparation of an aromatic aldehyde according to the present invention consists in introducing water into the reaction medium resulting from said condensation reaction, said reaction medium having or not having been separated beforehand, in heating the resulting aqueous medium at a temperature of between 10 and 200° C., in introducing the oxidation catalyst therein and in bubbling oxygen or air into said medium at atmospheric pressure or under pressure.

Another preferred embodiment of the process for the preparation of an aromatic aldehyde according to the present invention consists in carrying out the condensation and oxidation reactions under one-pot conditions, that is to say in one and the same reactor. A first one-pot embodiment consists in carrying out said condensation reaction and in then adding the oxidation catalyst to the reaction medium once said condensation reaction has been carried out. A second one-pot embodiment consists in bringing said aromatic compound(s) into contact with glyoxylic acid or its derivatives in a reaction medium comprising at least one catalyst providing the catalysis of the condensation and oxidation reactions, for example a condensation catalyst and an oxidation catalyst, said condensation and oxidation catalysts advantageously being chosen from those described in detail above in the present description. Said second embodiment can also be carried out in the presence of a single catalyst, which provides both the catalysis of the condensation reaction and then that of the oxidation reaction.

On conclusion of said oxidation reaction, the aromatic aldehyde(s) is/are obtained in an aqueous medium with various impurities. In order to separate the aromatic aldehyde(s) from the crude aqueous reaction mixture resulting from said oxidation reaction, said aromatic aldehyde(s) is/are advantageously extracted using an organic solvent. Said organic solvent dissolves said aromatic aldehyde(s) present in the aqueous medium. Recourse is advantageously had to an organic solvent which is inert with respect to the aromatic aldehyde(s). Mention may in particular be made, as solvents capable of being used, of halogenated or nonhalogenated aliphatic, cycloaliphatic or aromatic hydrocarbons, alcohols, ethers, ketones and nitriles. Mention is more particularly made, as aliphatic, cycloaliphatic or aromatic hydrocarbons, of heptane, cyclohexane, methylcyclohexane, benzene or toluene; as halogenated aliphatic, cycloaliphatic or aromatic hydrocarbons, of dichloromethane, trichloromethane, dichloroethane, chlorobenzene or dichlorobenzenes; as alcohols, of methanol, ethanol, propanol, isopropanol or butanol; as ethers, of diethyl ether, diisopropyl ether or methyl tert-butyl ether; as ketones, of acetone, methyl ethyl ketone, methyl isobutyl ketone or diisobutyl ketone; or, as nitriles, of acetonitrile. A mixture of said solvents can be used. The extraction operation is carried out at a temperature which depends on the nature of the solvent.

In order to isolate the aromatic aldehyde(s) from the extraction solvent, a separation can be carried out by recrystallization but, preferably, a distillation of said mixture is carried out which makes it possible to obtain, for example at the distillation top, the extraction solvent (if it is the most volatile compound of the mixture) and, for example at the distillation bottom, said aromatic aldehyde(s), namely a mixture comprising essentially said aromatic aldehyde(s), combined with heavy impurities and with small amounts of light impurities. Reference is made for this stage in particular to the process described in the patent application WO 2010/007161. The organic solvent used is advantageously recycled.

Optionally, the aromatic aldehyde(s) can be treated in order to condition it/them in solid form. Preferably, the aromatic aldehyde(s) purified, preferably by distillation, followed by crystallization (by use of one or more solvents or by the flaking technique), for example according to the following stages:

dissolution of said aromatic aldehyde(s) in a water-alcohol mixture (for example, methanol or ethanol);
vacuum crystallization;
pulling superficially dry batchwise;
drying of said aromatic aldehyde(s) at a temperature from 25° C. to a temperature below the melting point of said aromatic aldehyde(s), preferably under an inert gas (typically nitrogen).

Several alternative crystallization forms can be envisaged: for example batchwise crystallization, for example by cooling, or continuous crystallization, for example under vacuum.

Another subject matter of the present invention, independent of the other subject matters described above in the present description, is a process for the preparation of aromatic aldehyde(s) by oxidation of the corresponding mandelic derivative(s), said oxidation reaction being carried out in the presence of at least one oxidizing agent and of at least one catalyst and substantially in the absence of any acid or any base added to the reaction medium subjected to said oxidation reaction.

In accordance with the process for the preparation of aromatic aldehyde(s) by oxidation according to the invention, the term "mandelic derivative" is understood to mean an aromatic compound, at least one hydrogen atom of which directly bonded to the aromatic nucleus is replaced by a glycolic group of formula —CHOH—COOH. More particularly, the term "mandelic derivative" is understood to mean an aromatic compound, at least two hydrogen atoms of which directly bonded to the aromatic nucleus are replaced, one by a hydroxyl group and the other by a glycolic group of formula —CHOH—COOH. Said mandelic derivative(s) advantageously exhibit(s) the formula (II) explained above in the present description. It/They is/are obtained by condensation of at least one aromatic compound with glyoxylic acid or its derivatives. Said aromatic compound is advantageously chosen from those described above in the present description. Said condensation reaction is carried out in the presence of acid or base or substantially in the absence of any acid or any base added to the reaction medium. The term "substantially" is understood to mean the same maximum amount of acid or base specified above in the present description. Said oxidation reaction is carried out in the presence of a catalyst advantageously chosen from chromium, cobalt, copper, vanadium, manganese, iron, nickel and osmium derivatives. Preferably, vanadium and copper derivatives are chosen and, preferably, the catalyst employed for carrying out said oxidation reaction is ammonium metavanadate ($NH_4VO_3$) or vanadium oxide $V_2O_5$. Generally, the catalytic compound can be formed in situ during the reaction. For this reason, the term "catalyst" can also broadly comprise the precursors of these catalytic compounds.

The operating conditions for carrying out said oxidation reaction are in particular those described in the patent application WO 2008/148760.

Another subject matter of the present invention, independent of the other subject matters described above in the present description, is the use of a catalyst chosen from transition metal complexes comprising oxygen-comprising ligands, compounds based on rare earth metals, zeolites, clays, lanthanum phosphate, metal oxides and metal hydroxides in carrying out a condensation reaction in which an organic compound and a carbonyl compound are brought into contact substantially in the absence of any acid or any base added to the reaction medium, said condensation reaction not bringing about the coproduction of a simple molecule.

In accordance with the use according to the invention, said organic compound is an aromatic compound chosen from substituted benzenes, phenol and substituted phenols, heterocyclic aromatic compounds or polycyclic aromatic compounds. Said aromatic compounds described above in the present description are appropriate for said use. Said carbonyl compound generally comprises either an aldehyde functional group or a ketone functional group. Said metal complexes are used either by being supported or by being unsupported. The different metal complexes cited above in the present description are appropriate for catalyzing said condensation reaction.

Said condensation reaction employed for the use according to the invention is similar to an addition reaction of said organic compound to said carbonyl compound. Said reaction results in said addition product being obtained without coproduction of a simple molecule, such as water, hydrochloric acid, acetic acid, methanol or hydrogen sulfide.

The invention will be explained in more detail by means of the examples below, given by way of nonlimiting illustration.

EXAMPLES

Example 1

Preparation of Aromatic Compounds Carrying at Least One Mandelic Group by a Condensation Reaction of Glyoxylic Acid with an Aromatic Compound An amount of an aromatic compound is introduced into a 50 ml reactor provided with a temperature probe and with a mechanical stirrer and is heated to the temperature appearing in table 1. When the desired temperature is reached in the reactor, an amount of glyoxylic acid monohydrate in the solid form and a catalytic amount of Fe(acac)$_3$, that is to say an amount representing 2.5 mol % with respect to the limiting reactant, is introduced. In this example, considering that said aromatic compound and glyoxylic acid are employed according to an equimolar ratio, the amount of Fe(acac)$_3$ is such that it represents without distinction 2.5 mol % with respect to either of said two reactants. The reaction mixture is kept under magnetic stirring at the desired temperature for a period of time varying between 1 and 22 hours (cf table 1). At the end of the reaction, the products from the condensation reaction are assayed by high-performance liquid chromatography. The results obtained are collated in table 1.

| Aromatic compound | Phenol* | Guaiacol | Guaethol | o-Cresol | Veratrole | 1,2,3-Trimethoxy-benzene | Benzo-furan |
|---|---|---|---|---|---|---|---|
| Molar ratio Aromatic compound/ glyoxylic acid | 1 | 1 | 1 | 1 | 1 | 1 | 1 |
| T (° C.) | 45 | 45 | 45 | 45 | 45 | 45 | 80 |
| Duration (hour) | 20 | 3 | 5 | 1 | 22 | 22 | 20 |
| Conversion of the aromatic compound (%) | 87 | 85 | 85 | 85 | 35 | 75 | 75 |
| Yield of mandelic compound (%) | 75 | 60 | 50 | 62 | 19 | 37 | 70 |

*The condensation reaction carried out using phenol as aromatic compound was carried out in the presence of water as solvent according to a glyoxylic acid/water ratio by weight = 50/50.

The conversion of the aromatic compound corresponds to the ratio of the number of moles of aromatic compound consumed to the number of moles of aromatic compound employed.

The yield of mandelic compound corresponds to the ratio of the number of moles of mandelic compound formed to the number of moles of one or other of the reactants.

Example 2

1.5 mmol of guaiacol and 1.5 mmol of glyoxylic acid monohydrate are introduced into a 25 ml reactor equipped with a temperature probe and with a mechanical stirrer and heated at 50° C. on a water bath. No catalyst is added in this test. The reaction mixture is kept under magnetic stirring at 60° C. for 1 hour.

At the end of the reaction, the products from the condensation reaction are assayed by high-performance liquid chromatography. The conversion of guaiacol is 52% and the yield of mandelic compound is 30%.

Example 3

1.5 mmol of guaiacol, 1.5 mmol of glyoxylic acid monohydrate and 1 mol % of a catalyst are introduced into a 25 ml reactor equipped with a temperature probe and with a mechanical stirrer and heated at 50° C. on a water bath. The reaction mixture is kept under magnetic stirring at the desired temperature for 1 hour.

At the end of the reaction, the products from the condensation reaction are assayed by high-performance liquid chromatography. The results obtained are collated in the table below:

| | Catalyst | | | |
|---|---|---|---|---|
| | Fe(acac)$_3$ | Fe(acac)$_3$ | Cu(OAc)$_2$ | Cu(OAc)$_2$ |
| Temperature | 50° C. | 60° C. | 50° C. | 60° C. |
| Conversion of the aromatic compound (%) | 43 | 80 | 12 | 80 |
| Yield of mandelic compound (%) | 35 | 56 | 11 | 26 |

Example 4

Vanillylmandelic acid (1 mol/l) is introduced into an open, magnetically stirred, 8 ml vial containing a catalyst and a solvent. The concentration of catalyst is 1 mol %, with respect to the number of moles of vanillylmandelic acid. The reaction is carried out at 80° C. for 15 hours.

The yields of vanillin obtained, as a function of the catalyst and of the solvent used, are collated in the table below:

| Catalyst | Water | Isopropanol |
|---|---|---|
| V$_2$O$_5$ | 28 | 55 |
| NH$_4$VO$_3$ | 20 | 68 |
| VO(acac)$_2$ | 61 | 18 |
| Cu(OAc)$_2$ | 5 | 86 |

Example 5

Vanillylmandelic acid (0.1 mol/l) is introduced into a stirred reactor under O$_2$ pressure containing a catalyst (NH$_4$VO$_3$) and a solvent (water). The concentration of catalyst is 2.5 mol %, with respect to the number of moles of vanillylmandelic acid. The reaction is carried out at 80° C. under 7 bar for 180 minutes.

The degree of conversion of the vanillylmandelic acid is 100% and the yield of vanillin is 93%.

The invention claimed is:

1. A process for the preparation of one or more mandelic aromatic compounds carrying at least one mandelic —CHOH—COOH group comprising:

reacting at least one aromatic compound with glyoxylic acid or esters of glyoxylic acid under condensation conditions in the absence of any added acid or added base other than those constituted by reactants, an optional catalyst and an optional solvent, wherein the said aromatic compound is a substituted benzene substituted by one or more alkoxy groups, phenol or a substituted phenol according to formula (I):

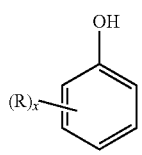

wherein:
R represents one or more identical or different substituents,
x, the number of substituents on a ring, is an integer between 1 and 4,
wherein R is selected from the group consisting of hydroxyl, linear or branched alkyl having from 1 to 6 carbon atoms, linear or branched alkoxy having from 1 to 6 carbon atoms and wherein a molar ratio of the said aromatic compound to glyoxylic acid or esters of glyoxylic acid varies from 0.9 to 1.1; and
recovering condensation products directly after the condensation reaction of the at least one aromatic compound with glyoxylic acid or esters of glyoxylic acid without intervening steps.

2. The process of claim 1, wherein said aromatic compound is a substituted phenol wherein the position para with respect to the hydroxyl group of the substituted phenol according to formula (I) is unsubstituted.

3. The process of claim 1, wherein the substituted phenols are selected from the group consisting of o-cresol, m-cresol, 3-ethylphenol, 2-(tert-butyl)phenol, guaiacol, and guaethol.

4. The process of claim 1, wherein the glyoxylic acid is in the monohydrate form.

5. The process of claim 1, wherein the step of reacting is carried out in the presence of at least one catalyst.

6. The process of claim 5, wherein the catalyst is selected from transition metal complexes comprising oxygen-comprising ligands.

7. The process of claim 5, wherein the catalyst is selected from the group consisting of: iron(II) acetate, iron(III) acetate, copper(II) acetate, iron(II) acetylacetonate, iron(III) acetylacetonate, copper(II) acetylacetonate, and copper(III) acetylacetonate.

8. The process of claim 5, wherein the catalyst comprises a complex composed of a transition metal and at least one glyoxylate ligand.

9. The process of claim 1, wherein the optional solvent is selected from the group consisting of water, aromatic hydrocarbons, alcohols, and water-alcohol mixtures.

10. The process of claim 1, wherein the process consists of reacting the glyoxylic acid with guaiacol, with guaethol, or with guaiacol and guaethol.

11. A process for the preparation of one or more mandelic aromatic aldehydes comprising:
reacting at least one aromatic compound with glyoxylic acid or esters of glyoxylic acid according to the process of claim 1 to prepare one or more mandelic aromatic compounds, and
oxidizing the one or more mandelic aromatic compounds.

12. The process of claim 11, wherein the step of oxidizing is carried out without addition of alkaline agent.

13. The process of claim 11, wherein the step of oxidizing is carried out in the presence of water as solvent.

14. The process of claim 11, wherein the step of oxidizing is carried out in the presence of a catalyst selected from the group consisting of chromium, cobalt, copper, vanadium, manganese, iron, nickel and osmium derivatives.

15. The process of claim 11, wherein the one or more aromatic aldehydes comprise vanillin, ethylvanillin, or vanillin and ethylvanillin.

16. The process of claim 1, wherein recovering the condensation products involves separation of mandelic aromatic compounds obtained from the condensation reaction by crystallization.

17. The process of claim 1, wherein recovering the condensation products involves separation of mandelic aromatic compounds obtained from the condensation reaction by extraction with at least an organic solvent.

18. The process of claim 1, wherein the reactor contents consist essentially of the reactants, the optional catalyst, the optional solvent, and an optional inert atmosphere.

* * * * *